(12) United States Patent
Cavan et al.

(10) Patent No.: US 9,128,064 B2
(45) Date of Patent: Sep. 8, 2015

(54) SUPER RESOLUTION INSPECTION SYSTEM

(71) Applicant: KLA-Tencor Corporation, Milpitas, CA (US)

(72) Inventors: Daniel L. Cavan, Woodside, CA (US); Grace Hsiu-Ling Chen, Los Gatos, CA (US); Qibiao Chen, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 3 days.

(21) Appl. No.: 13/863,519

(22) Filed: Apr. 16, 2013

(65) Prior Publication Data

US 2013/0321797 A1 Dec. 5, 2013

Related U.S. Application Data

(60) Provisional application No. 61/652,764, filed on May 29, 2012, provisional application No. 61/787,931, filed on Mar. 15, 2013.

(51) Int. Cl.
*G01N 21/95* (2006.01)
*G01N 21/88* (2006.01)

(52) U.S. Cl.
CPC ........ *G01N 21/9501* (2013.01); *G01N 21/8806* (2013.01); *G01N 2021/8835* (2013.01)

(58) Field of Classification Search
CPC .......... G01N 21/9501; G01N 21/8806; G01N 2021/8835
USPC ............ 356/237.1–237.5; 250/559.01, 559.4, 250/559.44, 216; 359/626, 668, 669
See application file for complete search history.

(56) References Cited

U.S. PATENT DOCUMENTS 4,619,508 A * 10/1986 Shibuya et al. ............... 353/122
4,974,919 A * 12/1990 Muraki et al. ............. 359/204.1
5,448,350 A * 9/1995 Kohno ....................... 356/237.2

(Continued)

FOREIGN PATENT DOCUMENTS

DE 102010018142 A1 12/2010
FR 2920869 A1 3/2009

(Continued)

OTHER PUBLICATIONS

G. Benjamin G. Eynon et. al. Photomask Fabrication Technology http://books.google.co.in/books?id=QCdxo8aTglYC&pg=PA366&lpg=PA366&dq=multi+parallel+TDI+Inspection+System&source=bl&ots=a59NIDaNzT&sig=B5kbYQokJ3hpj7qsdx1IXa3KiuU&hl=en&sa=X&ei=6VaqT4XOAoLKrAf8kvDSAQ&ved=0CF4Q6AEwAw#v=onepage&q=multi%20parallel%20TDI%20Inspection%20System&f=false.

(Continued)

*Primary Examiner* — Sang Nguyen
(74) *Attorney, Agent, or Firm* — Suiter Swantz pc llo

(57) ABSTRACT

The disclosure is directed to a system and method for inspecting a sample by illuminating the sample at a plurality of different angles and independently processing the resulting image streams. Illumination is directed through a plurality of pupil apertures to a plurality of respective field apertures so that the sample is imaged by portions of illumination directed at different angles. The corresponding portions of light reflected, scattered, or radiated from the surface of the sample are independently processed. Information associated with the independently processed portions of illumination is utilized to determine a location of at least one defect of the sample. Independently processing multiple image streams associated with different illumination angles allows for retention of frequency content that would otherwise be lost by averaging information from multiple imaging angles.

20 Claims, 12 Drawing Sheets

(56) References Cited

U.S. PATENT DOCUMENTS

| | | | |
|---|---|---|---|
| 5,734,470 A * | 3/1998 | Rogers et al. | 356/502 |
| 6,091,075 A * | 7/2000 | Shibata et al. | 250/559.44 |
| 6,621,571 B1 | 9/2003 | Maeda et al. | |
| 6,636,295 B2 * | 10/2003 | Shiozawa | 355/67 |
| 6,707,545 B1 | 3/2004 | Hunter | |
| 6,721,045 B1 | 4/2004 | Hunter | |
| 6,753,970 B1 | 6/2004 | Neumann et al. | |
| 6,921,905 B2 | 7/2005 | Shishido et al. | |
| 7,075,076 B2 | 7/2006 | Makino et al. | |
| 7,227,984 B2 | 6/2007 | Cavan | |
| 7,295,305 B2 | 11/2007 | Yoshida et al. | |
| 7,355,690 B2 | 4/2008 | Elyasaf et al. | |
| 7,359,044 B2 | 4/2008 | Nishiyama et al. | |
| 7,453,561 B2 | 11/2008 | Uto et al. | |
| 7,463,350 B2 | 12/2008 | Nishiyama et al. | |
| 7,535,562 B2 | 5/2009 | Matsui et al. | |
| 7,859,656 B2 | 12/2010 | Uto et al. | |
| 8,077,306 B2 | 12/2011 | Kawaguchi | |
| 8,120,001 B2 * | 2/2012 | Den Boef et al. | 250/559.01 |
| 8,138,475 B2 | 3/2012 | Wagner | |
| 8,160,351 B2 | 4/2012 | Sandström et al. | |
| 8,625,195 B2 * | 1/2014 | Lin et al. | 359/387 |
| 2003/0095251 A1 | 5/2003 | Maeda et al. | |
| 2005/0062963 A1 | 3/2005 | Yoshida et al. | |
| 2006/0072106 A1 | 4/2006 | Matsui et al. | |
| 2006/0290930 A1 | 12/2006 | Nishiyama et al. | |
| 2007/0052953 A1 | 3/2007 | Hill | |
| 2007/0195316 A1 | 8/2007 | Yoshida et al. | |
| 2008/0273196 A1 * | 11/2008 | Fairley et al. | 356/237.5 |
| 2009/0014649 A1 | 1/2009 | Nakasuji et al. | |
| 2009/0021723 A1 | 1/2009 | De Lega | |
| 2009/0147247 A1 | 6/2009 | Endo et al. | |
| 2009/0224151 A1 | 9/2009 | Hatakeyama et al. | |
| 2009/0231718 A1 * | 9/2009 | Muenz et al. | 359/626 |
| 2009/0263736 A1 | 10/2009 | Inoue et al. | |
| 2009/0284591 A1 | 11/2009 | Tsuchiya et al. | |
| 2010/0046853 A1 | 2/2010 | Goodnough et al. | |
| 2010/0104173 A1 | 4/2010 | Yoshida et al. | |
| 2010/0225903 A1 | 9/2010 | Nishiyama et al. | |
| 2010/0226495 A1 | 9/2010 | Kelly et al. | |
| 2010/0309308 A1 | 12/2010 | Saphier et al. | |
| 2011/0001972 A1 | 1/2011 | Shishido et al. | |
| 2011/0075928 A1 | 3/2011 | Jeong et al. | |
| 2011/0115793 A1 | 5/2011 | Grycewicz | |
| 2011/0291165 A1 | 12/2011 | Eckardt | |
| 2011/0304725 A1 | 12/2011 | Sakai et al. | |
| 2012/0127331 A1 | 5/2012 | Grycewicz | |

FOREIGN PATENT DOCUMENTS

| | | |
|---|---|---|
| JP | 4192118 B2 | 7/1992 |
| JP | 2000-241349 A | 9/2000 |
| JP | 2005083800 A | 3/2005 |
| JP | 4716419 B2 | 11/2005 |
| JP | 3858571 B2 | 9/2006 |
| JP | 3965325 B2 | 6/2007 |
| JP | 4883618 B2 | 2/2008 |
| JP | 2011221499 A | 11/2011 |
| WO | 0023986 A1 | 4/2000 |
| WO | 0023986 A1 | 5/2001 |
| WO | 2006019446 A2 | 2/2006 |
| WO | 2006019446 A3 | 2/2006 |
| WO | 2009026522 A1 | 2/2009 |
| WO | 2009030698 A1 | 3/2009 |
| WO | 2009090633 A2 | 7/2009 |
| WO | 2011106821 A1 | 9/2011 |
| WO | 2012056192 A1 | 5/2012 |

OTHER PUBLICATIONS

Yakov Bulayev TDI Imaging: An Efficient AOI and AXI Tool http://www.ipcoutlook.org/pdf/tdi_imaging_ipc.pdf.

Bo-Jui Chang, et al. Subdiffraction scattered light imaging of gold nanoparticles using structured illumination vol. 36, No. 24, Optics Letters, Dec. 15, 2011, Optical Society of America, pp. 4773-4775.

Christian Maurer, et al. Tailoring of arbitrary optical vector beams New Journal of Physics 9 (2007) 78, IOP Publishing Ltd and Deutsche Physikalische Gesellschaft Online at http://www.njp.org.

S. Usuki, et al. Development of super-resolution optical inspection system for semiconductor defects using standing wave illumination shift Proc. of SPIE vol. 6375 637508 (2006).

Katherine Speichinger "Structured Illumination", Physics 598: Optical Microscopy, Mar. 8, 2010.

Oren Haik et al., Superresolution reconstruction of a video captured by a vibrated time delay and integration camera, Journal of Electronic Imaging 15(2), pp. 023006-1-023006-12 (Apr.-Jun. 2006).

Reinhold Huber-Mork et al., Image Super-Resolution for Line Scan Cameras based on a Time Delay Super-Resolution Principle, Proceedings of the 6th International Symposium on Image and Signal Processing and Analysis, Sep. 2009, pp. 129-134.

Gadi Hochman, et al., Restoration of images captured by a staggered time delay and integration camera in the presence of mechanical vibrations, Applied Optics, vol. 43, No. 22, Aug. 1, 2004, pp. 4345-4354, © Optical Society of America.

L N Hazra et al., Super-resolution by pupil plane phase filtering, Pramana—journal of physics, vol. 75, No. 5, Nov. 2010, pp. 855-867, © Indian Academy of Sciences.

Riichi Nagura, Accurate 3D information extraction from large-scale data compressed image and the study of the optimum stereo imaging method, International Archives of the Photogrammetry, Remote Sensing and Spatial Information Sciences, vol. XXXIV-5/W10, 9 pages, Printed online Apr. 22, 2015.

* cited by examiner

SUPER RESOLUTION INSPECTION SYSTEM

PRIORITY

The present application claims priority to the following U.S. Provisional Applications:

Ser. No. 61/652,764, entitled FAST SUPER RESOLUTION TDI INSPECTION SYSTEM, By Dan Cavan et al., filed May 29, 2012; and Ser. No. 61/787,931, entitled MULTIPLE-ANGLE INSPECTION SYSTEM, By Daniel L. Cavan et al., filed Mar. 15, 2013.

TECHNICAL FIELD

The present disclosure generally relates to the field of sample inspection and more particularly to improving inspection resolution by independently imaging the sample at a plurality of different angles.

BACKGROUND

In modern manufacture and testing of semi-conductor devices, inspection systems are employed at various stages to locate and assess defects of a sample such as, but not limited to, a silicon wafer or a mask. According to various systems and methods known in the art, the sample may be illuminated utilizing a large pupil aperture such that defect information associated with illumination reflected, scattered, or radiated from the sample includes averaged content from all scattering angles. Information content from angles at which a sample defect strongly scatters illumination may be substantially attenuated as a result of the averaging, leading to a loss of inspection resolution. There is a need in the art for systems and methods of inspecting a sample without the foregoing limitations.

SUMMARY

A sample defect typically emits light beyond detection capability of an optical inspection system. However, data obtained at different oblique illumination angles may be combined to enhance the effective optical resolution of a system. In one aspect, the disclosure is directed to a system for inspecting a sample by illuminating the sample with narrowband or broadband illumination at a plurality of different angles and independently processing the resulting image streams.

According to various embodiments, the system includes a stage configured to support a sample and at least one illumination source configured to illuminate the sample by providing illumination along an illumination path. A plurality of pupil apertures are configured to substantially simultaneously or sequentially receive illumination directed along a first portion of the illumination path. The illumination is directed through each pupil aperture along a second portion of the illumination path to a respective field aperture. In some embodiments, portions of illumination are directed in parallel from each of the pupil apertures to a respective field aperture of a plurality of field apertures for parallel imaging by utilizing a plurality of overlaid prisms or a functionally equivalent set of light bending optical elements. In other embodiments, illumination is directed through each pupil aperture independently along a path to the field aperture for sequential imaging. The one or more field apertures are configured to direct illumination received from the pupil apertures along a third portion of the illumination path to a surface of the sample.

The system further includes one or more detectors configured to receive portions of light reflected, scattered, or radiated from the surface of the sample, where each portion of illumination is associated with a respective pupil aperture. At least one computing system in communication with the one or more detectors is configured to independently process each portion of the light received by the one or more detectors. The computing system is further configured to determine a location of at least one defect of the sample utilizing information associated with the independently processed images arriving at each of the detectors, thus allowing for retention of frequency content (i.e. higher resolution) that would otherwise be lost if the detector outputs were averaged.

In some embodiments, a plurality of detectors (operating in parallel) may be configured to substantially simultaneously receive portions of the light reflected, scattered, or radiated from the surface of the sample. For example, a plurality of prisms may be configured to direct a portion of the light collected from the sample surface to each of the detectors. Each detector may be further configured to receive a portion of the light associated with a respective pupil aperture, thus enabling parallel imaging of the sample at different illumination angles. The computing system may be further configured to independently process the image streams in parallel for high resolution inspection at an increased speed.

In another aspect, the disclosure is directed to a method of inspecting a sample in accordance with embodiments of the system described herein. However it is noted that one or more steps of the method may be executed by additional or alternative configurations beyond those described with regard to embodiments of the system. The method should be understood to include any arrangement of components configured to execute the steps and/or functions described in further detail below.

According to various embodiments, the method includes at least the following steps: providing illumination along an illumination path; receiving illumination directed along a first portion of the illumination path utilizing a plurality of pupil apertures; directing portions of the illumination from the plurality of pupil apertures along a second portion of the illumination path to one or more field apertures; directing portions of illumination from the one or more field apertures along a third portion of the illumination path to a surface of a sample; receiving portions of illumination reflected, scattered, or radiated from the surface of the sample utilizing one or more detectors, each portion of illumination being associated with a respective pupil aperture; independently processing each portion of illumination received by the one or more detectors; and determining a location of at least one defect of the sample utilizing information associated with the independently processed portions of illumination.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings.

The resolution of an optical system is proportional to $\lambda/NA$, where $\lambda$ is wavelength of illumination and NA is numerical aperture of the optics. One method of resolution enhancement is to decrease $\lambda$ and/or increase NA. However, in the current state of the art, light source and optical design development are pushed to a limit where reducing $\lambda$ or increasing NA of the system is increasingly challenging. The disclosure is directed to a system and method enabling increased optical resolution without requiring manipulation of $\lambda$ and/or NA.

Figure 1A:
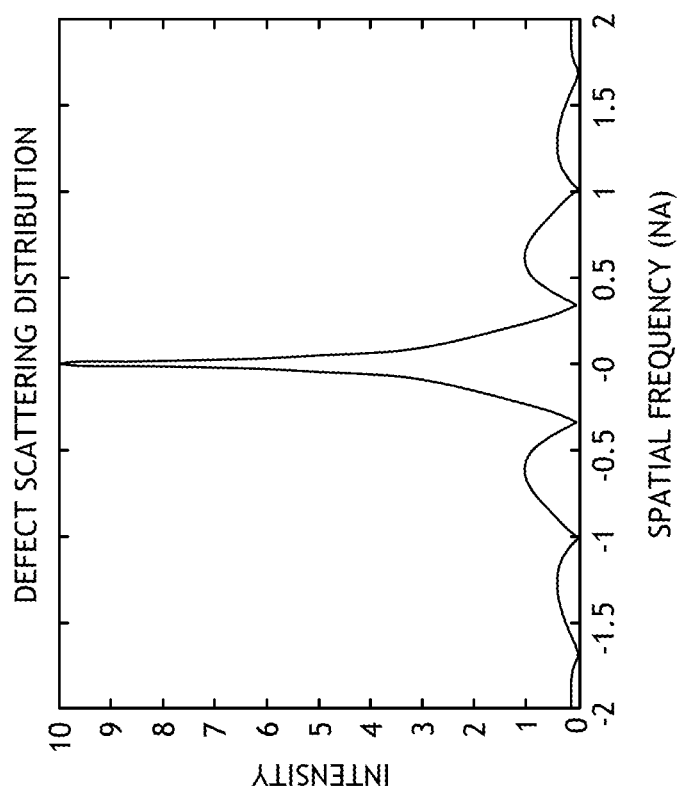
FIG. 1A illustrates an example of defect scattering information of an illuminated wafer expressed in the spatial frequency domain.
Figure 1B:
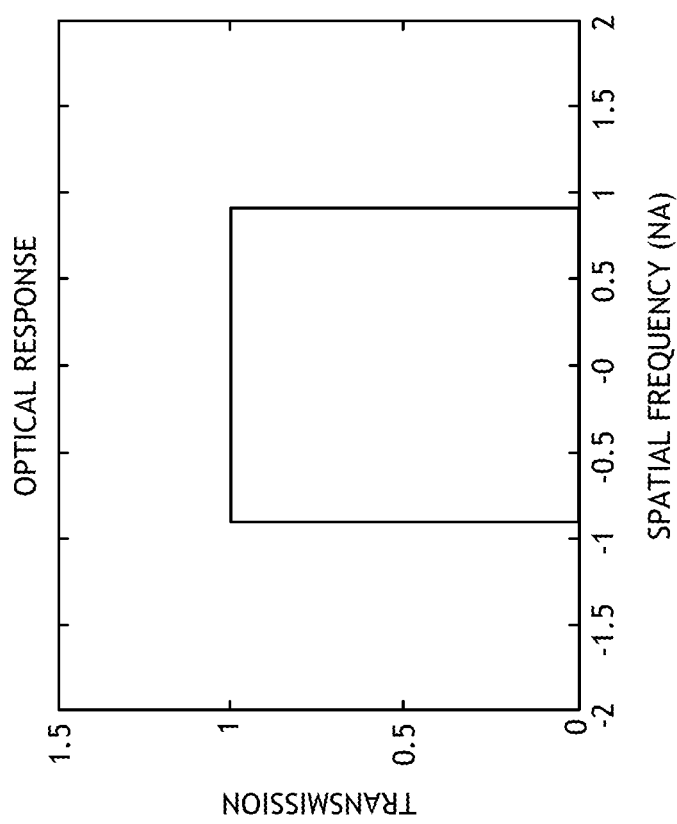
FIG. 1B illustrates a range of detection for a typical defect inspection system expressed in the spatial frequency domain.
Figure 1C:
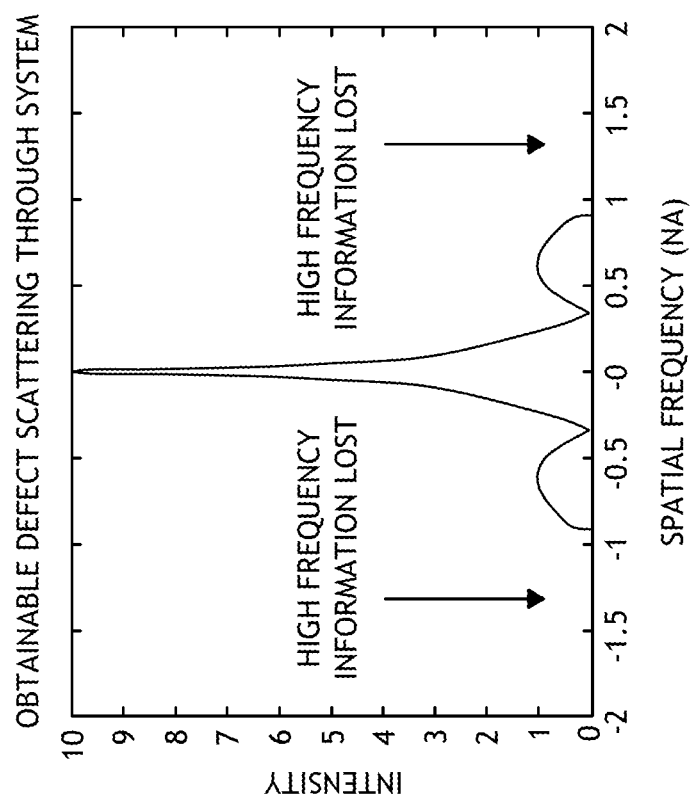
FIG. 1C illustrates a detectable range of defect scattering information expressed in the spatial frequency domain.

A sample defect typically emits light beyond a range capable of being collected by an optical inspection system. FIG. 1A shows an example of a defect scattering signal expressed in the spatial frequency domain. In the example, the scatter of the defect is extended up to $\pm 2$ NA. Since a typical high precision optical system can generally detect up to $\pm 0.9$ NA (as illustrated in FIG. 1B), the defect scattering information beyond $\pm 0.9$ NA is not attainable. FIG. 1C shows an example of the attainable defect scattering information for such a system.

Figure 2A:
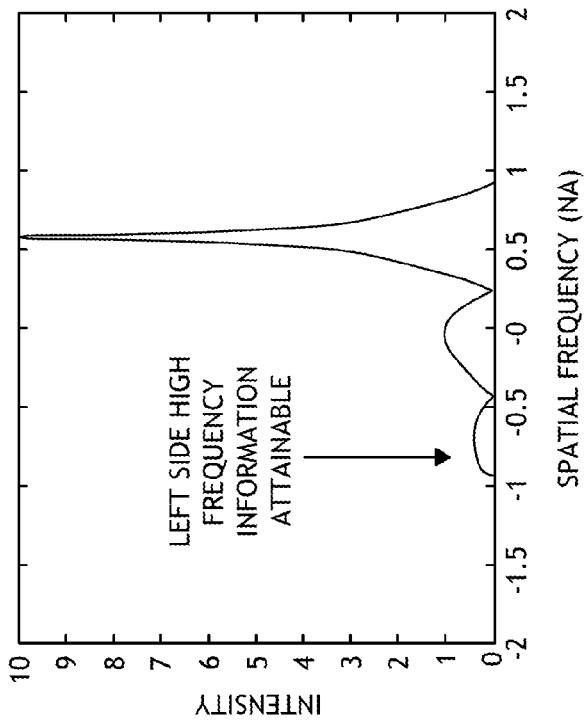
FIG. 2A illustrates a wafer being illuminated at a first oblique angle, in accordance with an embodiment of this disclosure.
Figure 2A:
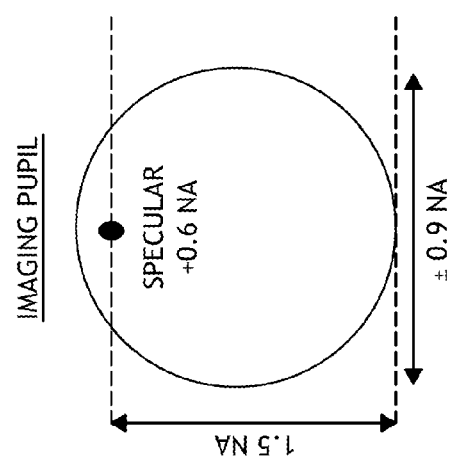
Figure 2A:
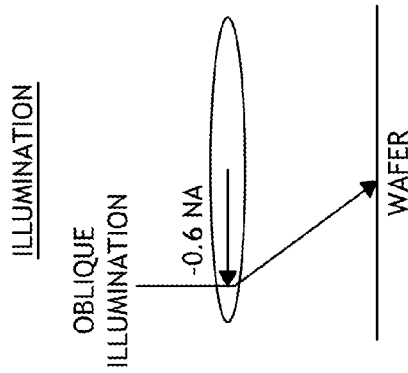
Figure 2B:
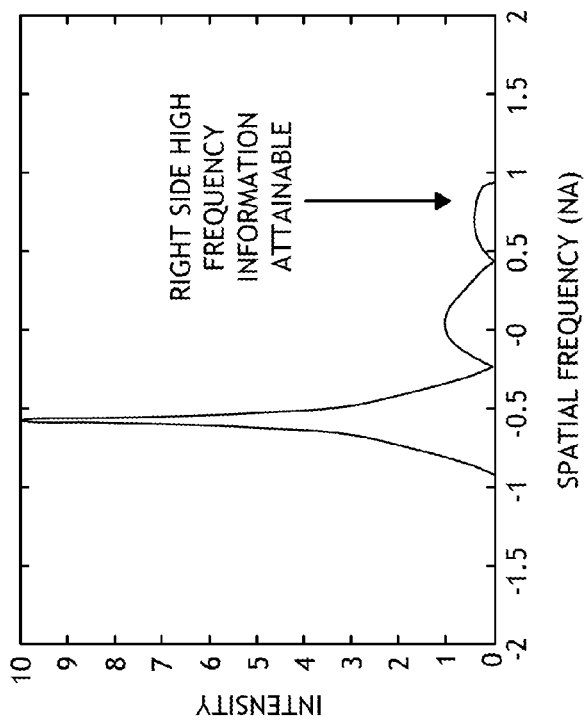
FIG. 2B illustrates the wafer being illuminated at a second oblique angle, in accordance with an embodiment of this disclosure.
Figure 2B:
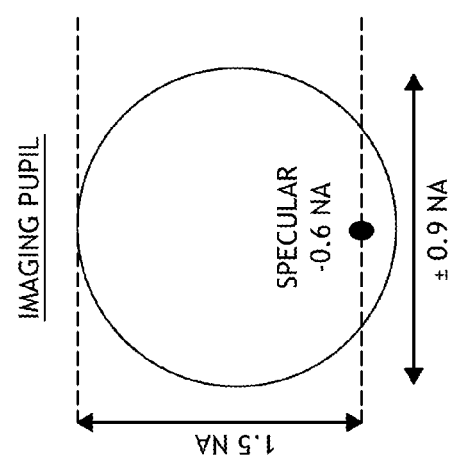
Figure 2B:
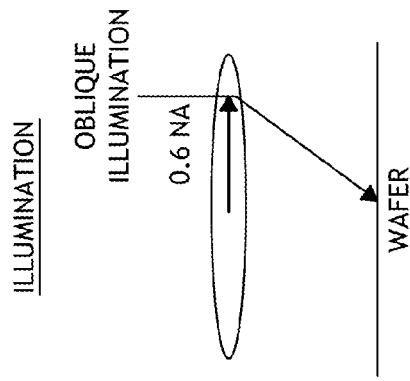

However, the defect scattering distribution will be shifted if the sample is illuminated at an oblique angle. As a result, the system may detect scattering information at higher NA. FIGS. 2A and 2B illustrate a wafer being illuminated at a first oblique angle and a second oblique angle, respectively. In FIG. 2A, the illumination is shifted such that the beam is illuminated from $-0.6$ NA. By doing so, the specular beam is shifted to $+0.6$ NA, and the maximum NA from the specular point to the end of the optical lens is now extended from 0.9 NA to 1.5 NA. The right hand side shows how the defect scattering distribution is shifted accordingly. Because of the spectrum shift, higher NA defect info from the left is now allowed in the optical system. FIG. 2B shows the effect of illuminating the defect obliquely from the opposite direction to that shown in FIG. 2A.

Figure 3:
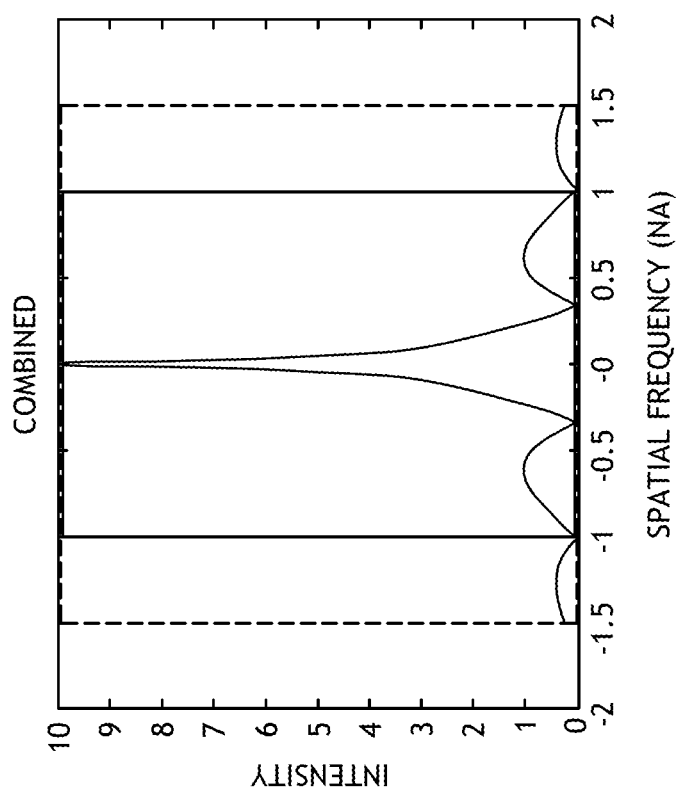
FIG. 3 illustrates a detectable range of defect scattering information expressed in the spatial frequency domain for the wafer including scattering information obtained by illuminating the wafer at the first oblique angle combined with information obtained by illuminating the wafer at the second oblique angle, in accordance with an embodiment of this disclosure.

Resolution is enhanced by combining data obtained at a plurality of different oblique illumination angles. FIG. 3 shows how the results from two different oblique angles can be combined such that the range of information detected by the system is effectively greater than $\pm 0.9$ NA. As a result, the effective optical resolution of the system is enhanced. It is noted herein that the foregoing exemplary values and ranges are provided for illustrative purposes only and are not intended to limit the present disclosure in any way.

FIGS. 4 through 7 generally illustrate a system and method for inspecting a sample by processing a plurality of image streams collected at different illumination angles. By illuminating the sample at high angles and then independently processing each high angle image of the sample, defect information may be collected at a higher signal-to-noise ratio (SNR). In some applications, the improved sensitivity offered by this high angle illumination may allow detection of defects approximately half the size of defects detected by other systems existing in the art. Resolution of the inspection system is enhanced by independently inspecting multiple images of a sample, each image taken with a different high angle illumination. Hence, the system may be referred to as a "super resolution" inspection system. The system and method described herein may be configured for small pixel or well sampled brightfield applications; however, it is contemplated that various configurations or techniques described herein may be extended to further applications as well.

As used throughout the present disclosure, the term "sample" generally refers to a substrate formed of a semiconductor or non-semiconductor material which may include one or more "layers" or "films" formed thereon. For example, semiconductor or non-semiconductor materials include, but are not limited to, monocrystalline silicon, gallium arsenide, and indium phosphide. Layers formed on the substrate may include, but are not limited to, a resist, a dielectric material, a conductive material, or a semiconductive material. Many different types of sample layers are known in the art, and the term sample as used herein is intended to encompass a substrate and any types of layers which may be formed thereon.

Figure 4:
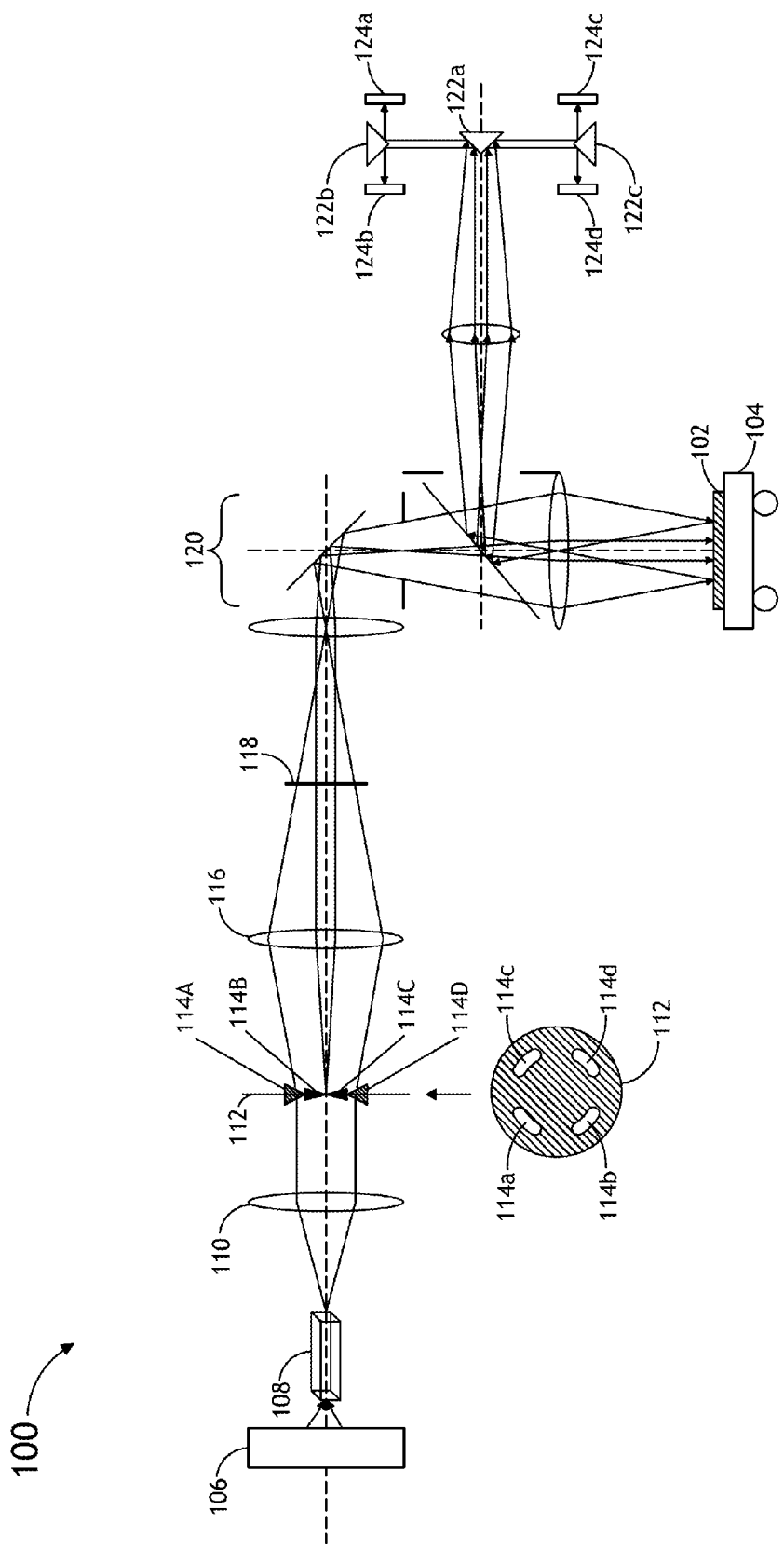
FIG. 4 is a block diagram illustrating an inspection system, in accordance with an embodiment of this disclosure.

FIG. 4 illustrates a system 100 for inspecting a sample 102 by independently processing image streams collected at different illumination angles, in accordance with an embodiment of the disclosure. The system 100 includes a stage 104 configured to support the sample 102 for inspection. In some embodiments, the stage 104 is further configured to actuate the sample 102 to a selected position or orientation. Accordingly, the stage 104 may include or may be mechanically coupled to at least one actuator, such as a motor or servo configured to translate or rotate the stage 104.

The system 100 includes at least one illumination source 106 configured to provide broadband or narrowband illumination along an illumination path defined by a series of optical elements. In some embodiments, the illumination path may include a homogenizer 108 configured to scramble illumination frequencies to achieve substantially uniform illumination intensity along the illumination path. The illumination path may further include at least a first lens 110 configured to focus illumination onto an illumination pupil 112 and a second lens 116 configured to focus illumination onto an imaging field 118. The system 100 may further include an objective lens assembly 120 configured to direct illumination from the imaging field 118 to a surface of the sample 102 and further configured to direct light reflected, scattered, or radiated from the surface of the sample 102 along a collection path to one or more detectors 124 such as, but not limited to, time delay integration (TDI) cameras or sensor arrays.

In an embodiment, the pupil 112 includes a plurality of apertures configured to substantially simultaneously receive illumination directed along a first portion of the illumination path. Each pupil aperture is further configured to direct a portion of illumination through a respective prism 114 or equivalent light bending optical element. The prisms 114 are configured to direct the respective portions of illumination from the plurality of pupil apertures along a second portion of the illumination path to corresponding field apertures, where each pupil aperture and field aperture pair is associated with a respective illumination angle. In some embodiments, the pupil plane further includes the plurality of prisms 114 disposed proximate to (e.g. overlaid on to) the pupil apertures. Each field aperture is configured to direct a portion of illumination received from a respective pupil aperture along a third portion of the illumination path to the surface of the sample 102 at a different illumination angle defined by the respective pupil aperture.

Figure 5A:
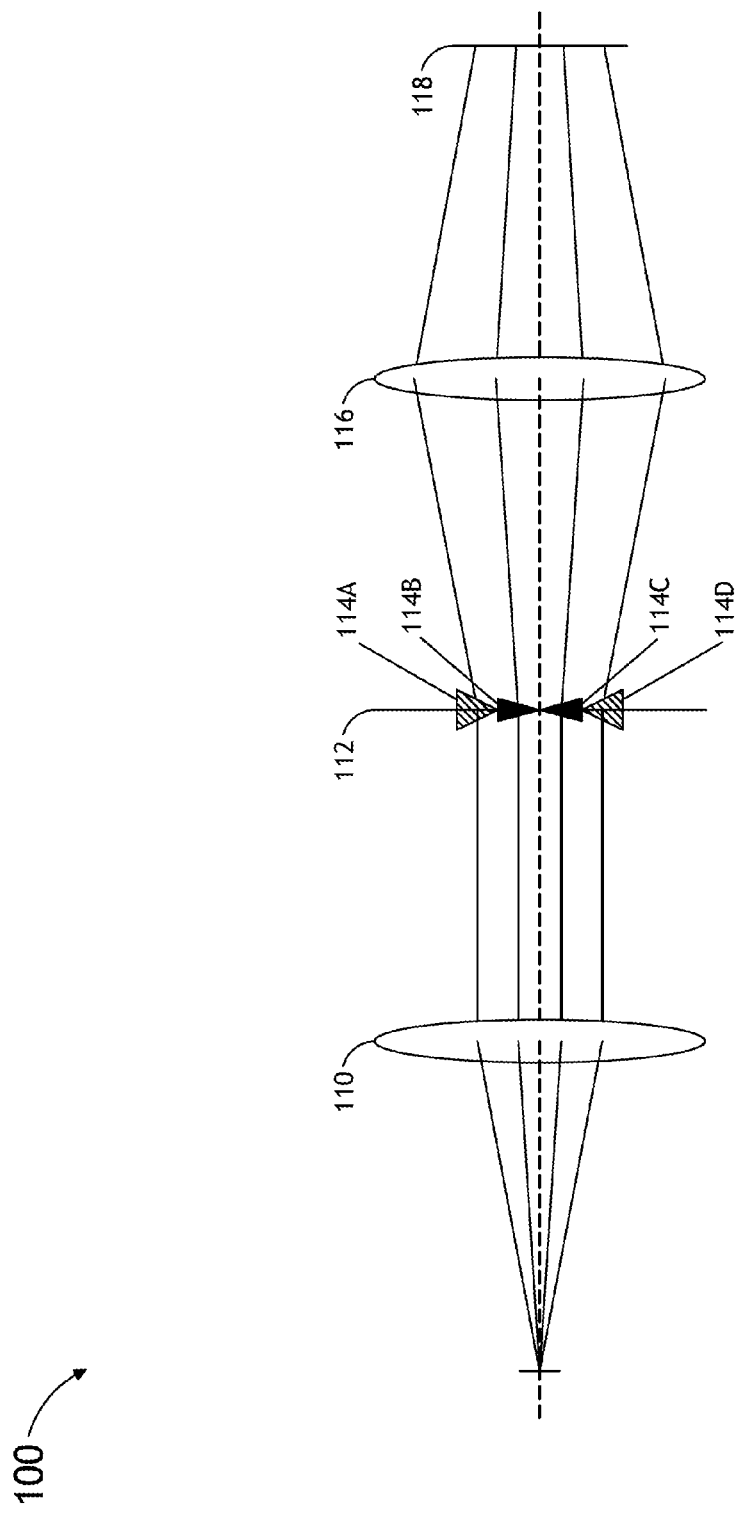
FIG. 5A is a block diagram illustrating a portion of the inspection system, wherein portions of illumination are directed from a plurality of pupil apertures to a plurality of respective field apertures, in accordance with an embodiment of this disclosure.
Figure 5B:
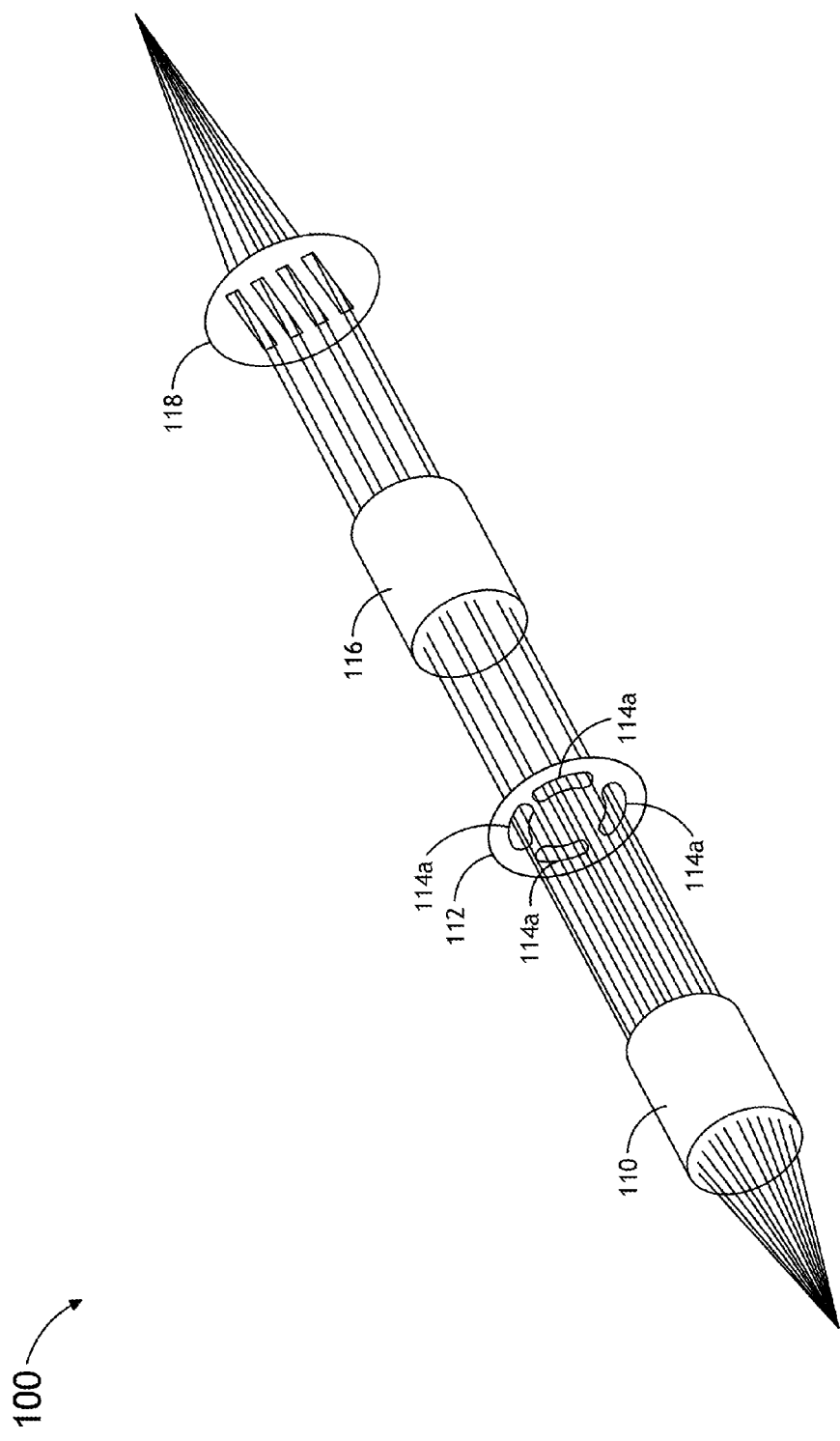
FIG. 5B is a perspective view illustrating the portion of the inspection system, wherein portions of illumination are directed from the plurality of pupil apertures to the plurality of respective field apertures, in accordance with an embodiment of this disclosure.
Figure 6A:
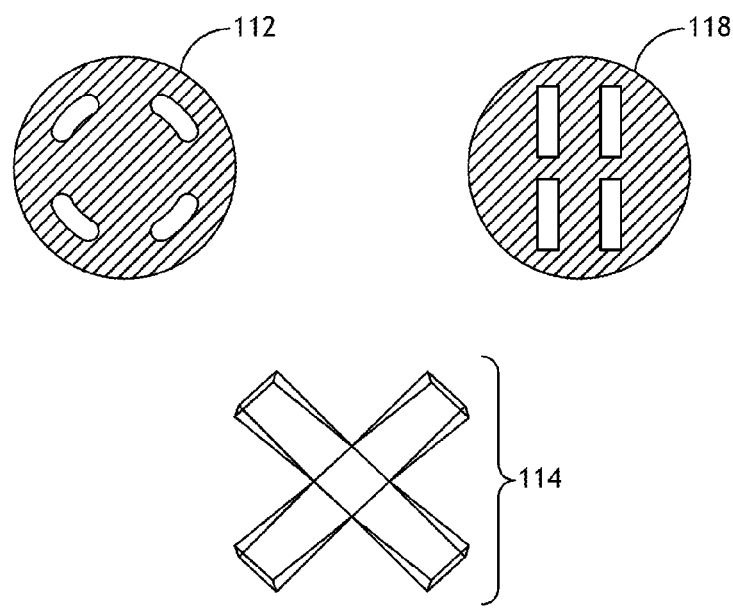
FIG. 6A illustrates a pupil, a field, and an array of prisms for directing portions of illumination form a plurality of pupil apertures to a plurality of respective field apertures, in accordance with an embodiment of this disclosure.
Figure 6B:
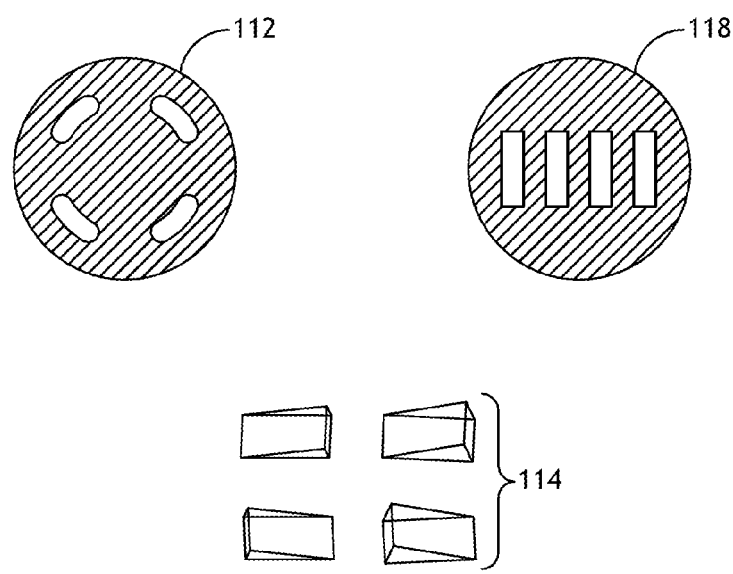
FIG. 6B illustrates a pupil, a field, and an array of prisms for directing portions of illumination form a plurality of pupil apertures to a plurality of respective field apertures, in accordance with an embodiment of this disclosure.
Figure 6C:
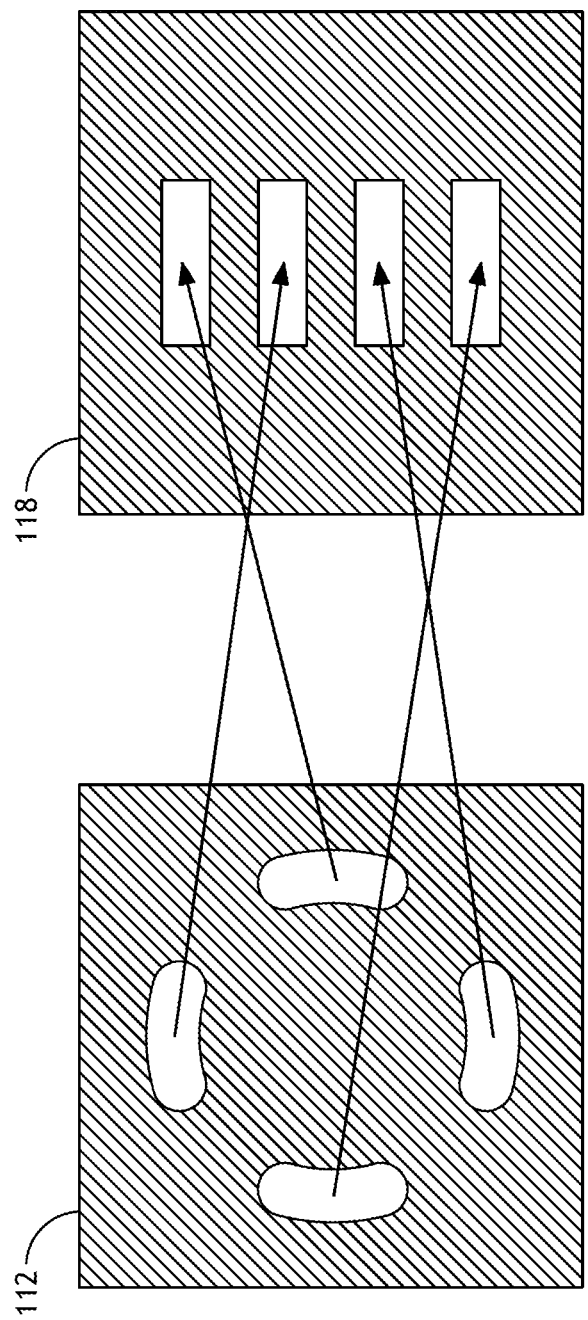
FIG. 6C illustrates an illumination mapping between a plurality of pupil apertures and a plurality of field apertures, in accordance with an embodiment of this disclosure.

FIGS. 5A and 5B illustrate an embodiment, where prisms 114 are overlaid on each aperture of the pupil 112 allowing illumination streams to flow from the pupil apertures to respective field apertures in parallel to allow for simultaneous imaging of the sample 102 at different illumination angles. FIGS. 6A and 6B further illustrate the pupil 112, overlay prisms 114, and the respective field 118 in accordance with various embodiments of the system 100. FIG. 6C further illustrates an exemplary mapping between portions of illumination flowing through pupil apertures to respective field apertures. When the system 100 relies upon broadband illumination, an oversized homogenizer 108 may be utilized to accommodate for spectral blurring.

The system 100 may further include a plurality of detectors 124, each configured to receive light scattered, reflected, or radiated from the sample 102 at an angle associated with a respective pupil aperture and field aperture pair. At least one computing system communicatively coupled to the detectors 124 may be configured to locate defects of the sample 102 by independently processing the portions of the light (i.e. image stream) collected by each detector 124. For example, the computing system may be configured to run an inspection algorithm on an each image from each of the detectors 124 independently to search for defects. The independent processing may avoid loss of resolution to due to averaging of frequency content when detector outputs are combined into a single image.

In some embodiments, the computing system may be configured to employ a voting algorithm where a defect is declared when the defect is located in at least two of the detector channels. Thus, the computing system may be configured to inspect for defects without needing to combine detector outputs. The detector outputs may be independently (or at least partially independently) processed according to alternative algorithms known to the art without deviating from the present disclosure. The foregoing voting algorithm is included for illustrative purposes and is not intended to limit the disclosure in any way.

It should be recognized that the various steps and functions described throughout the present disclosure may be carried out by a single computing system or by multiple computing systems. The one or more computing systems may include, but are not limited to, a personal computing system, mainframe computing system, workstation, image computer, parallel processor, or any other device known in the art. In general, the term "computing system" may be broadly defined to encompass any device having at least one single-core or multiple-core processor configured to execute program instructions from at least one carrier medium.

In some embodiments, the system 100 includes four pupil apertures, overlaid prisms 114, and four field apertures configured to generate four image streams resulting from quadruple illumination of the sample 102. The system 100 may further include four detectors 124 configured to collect the image streams substantially simultaneously for parallel processing. It may be advantageous to further provide for greater than four image streams. In some embodiments, for example, the system 100 may include eight pupil and field aperture pairs and eight detectors 124 configured to collect the resulting image streams.

In some embodiments, parallel illumination at different angles may be achieved by alternative configurations. For example, multiple narrowband illumination sources or a single illumination source 106 with a beam splitter may be configured to provide illumination along a plurality of paths each including a pupil having an aperture disposed according to a selected angle.

Parallel illumination and processing allows for rapid sample inspection. In some embodiments, however, super resolution may be achieved by sequentially collecting image streams at different angles and/or by sequentially (but independently) processing each image stream. As such, the pupil apertures may be sequentially illuminated. For example, a plurality of pupils may be sequentially actuated through the illumination path where each pupil includes an aperture disposed according to a selected illumination angle. Alternatively, the pupil 112 may be rotated through the illumination path one aperture at a time or partially covered so that one aperture is illuminated at each image of the sample. Accordingly, the plurality of pupil apertures may be configured to sequentially direct illumination at different angles to a field aperture without requiring overlaid prisms 114 or a functionally equivalent optical element.

Furthermore, a single detector may be configured to collect each of the resulting image streams sequentially or each of the plurality of detectors 124 may be configured to collect the resulting image streams in sequence. As illustrated by the foregoing examples, the system 100 may be implemented according to several variations from the embodiments described above without departing from the scope of this disclosure.

Figure 7:
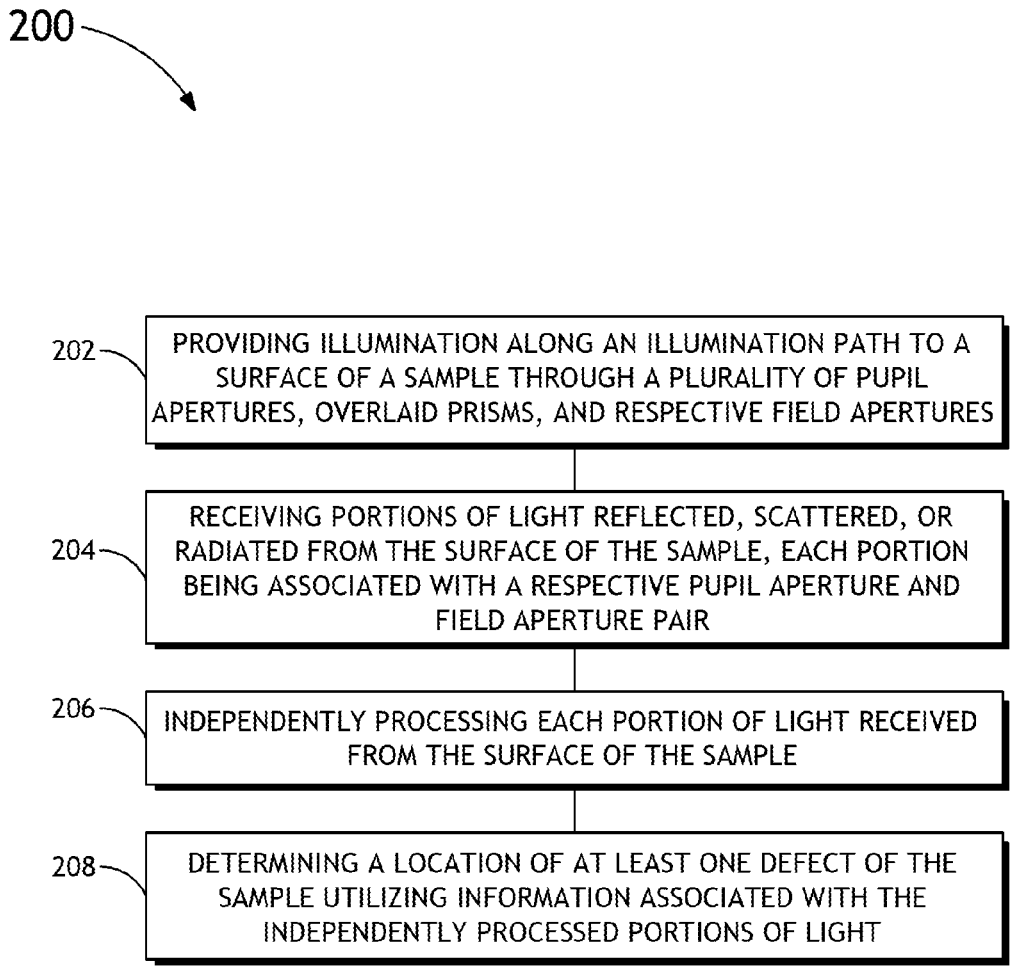
FIG. 7 is a flow diagram illustrating a method of inspecting a sample, in accordance with an embodiment of this disclosure.

FIG. 7 is a flow diagram illustrating a method 200 of inspecting a sample in accordance with the foregoing system 100. However, one or more steps of method 200 may be executed by optical configurations varying from those described with regard to embodiments of system 100. The method 200 is intended to encompass any system or configuration now or hereafter known to the art for carrying out the following steps. Furthermore, the method 200 may include steps for carrying out any function described with regard to system 100 that is not explicitly listed below.

At step 202, illumination is provided along an illumination path sequentially or substantially simultaneously to a plurality of pupil apertures. In some embodiments, portions of the illumination are directed in parallel through each of the pupil apertures and overlaid prisms 114 along a second portion of the illumination path to respective field apertures, where each pupil and field aperture pair are associated with a selected illumination angle. The portions of illumination resulting from each pupil aperture and field aperture pair are further directed along a third portion of the illumination path to a surface of a sample 102. At step 204, portions of light reflected, scattered, or radiated from the surface of the sample 102 (i.e. image streams) are collected utilizing one or more detectors 124. Each image stream is associated with a different illumination angle resulting from manipulation by a respective pupil aperture. At step 206, each image stream associated with a particular set of illumination angles is independently processed. At step 208, the independently processed image streams are utilized to determine a location of at least one defect of the sample 102, thereby allowing for improved defect resolution due to retained frequency content that would otherwise be lost if the information associated with each image stream were combined into an averaged defect signal.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. Program instructions implementing methods such as those described herein may be transmitted over or stored on carrier media. A carrier medium may include a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. A system for inspecting a sample, comprising:
   a stage configured to support a sample;
   at least one illumination source configured to provide illumination along an illumination path;
   a plurality of pupil apertures, each configured to receive illumination directed along a first portion of the illumination path, and further configured to direct a portion of the illumination along a second portion of the illumination path;
   one or more field apertures configured to receive a portion of illumination directed along the second portion of the illumination path by a respective pupil aperture of the plurality of pupil apertures, and further configured to direct the portion of illumination along a third portion of the illumination path to a surface of the sample from at least two different illumination angles;
   one or more detectors configured to receive portions of illumination reflected, scattered, or radiated from the surface of the sample, each portion of illumination reflected, scattered, or radiated from the surface of the sample being associated with a respective pupil aperture of the plurality of pupil apertures; and
   at least one computing system in communication with the one or more detectors, the computing system configured to independently process each portion of illumination reflected, scattered, or radiated from the surface of the sample to independently conduct defect detection for said at least two different illumination angles, and the computing system further configured to determine a location of at least one defect of the sample utilizing information associated with the independently processed portions of illumination.

2. The system of claim 1, wherein the plurality of pupil apertures are configured to be sequentially rotated through the illumination path.

3. The system of claim 1, wherein the plurality of pupil apertures are configured to substantially simultaneously receive illumination.

4. The system of claim 3, further comprising:
   a plurality of prisms disposed proximate to the plurality of pupil apertures, each prism configured to direct a portion of illumination from a respective pupil aperture along the second portion of the illumination path to a respective field aperture.

5. The system of claim 1, wherein the plurality of pupil apertures includes at least four pupil apertures, and the plurality of field apertures includes at least four field apertures.

6. The system of claim 1, wherein the one or more detectors comprise one or more time delay integration cameras.

7. The system of claim 1, wherein the one or more detectors comprise one detector configured to sequentially receive portions of illumination reflected, scattered, or radiated from the surface of the sample.

8. The system of claim 1, wherein the one or more detectors comprise a plurality of detectors configured to substantially simultaneously receive portions of illumination reflected, scattered, or radiated from the surface of the sample.

9. The system of claim 8, wherein the plurality of detectors includes at least four detectors.

10. The system of claim 8, further comprising:
    a plurality of prisms configured to direct portions of illumination reflected, scattered, or radiated from the surface of the sample to the plurality of detectors.

11. A system for inspecting a sample, comprising:
    a stage configured to support a sample;
    at least one illumination source configured to provide illumination along an illumination path;
    a plurality of pupil apertures configured to substantially simultaneously receive illumination directed along a first portion of the illumination path;

a plurality of prisms disposed proximate to the plurality of pupil apertures, each prism configured to direct a portion of illumination from a respective pupil aperture along the second portion;

a plurality of field apertures configured to substantially simultaneously receive portions of illumination directed along the second portion of the illumination path by the plurality of prisms, each field aperture configured to receive a portion of illumination from a respective pupil aperture of the plurality of pupil apertures, and further configured to direct the portion of illumination along a third portion of the illumination path to a surface of the sample from at least two different illumination angles;

a plurality of detectors configured to substantially simultaneously receive portions of illumination reflected, scattered, or radiated from the surface of the sample, each detector configured to receive a portion of illumination reflected, scattered, or radiated from the surface of the sample associated with a respective pupil aperture of the plurality of pupil apertures; and at least one computing system in communication with the plurality of detectors, the computing system configured to independently process the portion of illumination received by each detector to independently conduct defect detection for said at least two different illumination angles, and the computing system further configured to determine a location of at least one defect of the sample utilizing information associated with the independently processed portions of illumination.

12. The system of claim 11, wherein the plurality of pupil apertures includes at least four pupil apertures, the plurality of field apertures includes at least four field apertures, and the plurality of detectors includes at least four detectors.

13. The system of claim 11, wherein the plurality of detectors comprises a plurality of time delay integration cameras.

14. The system of claim 11, further comprising:
a plurality of prisms configured to direct portions of illumination reflected, scattered, or radiated from the surface of the sample to the plurality of detectors.

15. A method of inspecting a sample, comprising:
providing illumination along an illumination path;
receiving illumination directed along a first portion of the illumination path utilizing a plurality of pupil apertures;
directing portions of the illumination from the plurality of pupil apertures along a second portion of the illumination path to one or more field apertures;
directing portions of illumination from the one or more field apertures along a third portion of the illumination path to a surface of a sample from at least two different illumination angles;
receiving portions of illumination reflected, scattered, or radiated from the surface of the sample utilizing one or more detectors, each portion of illumination being associated with a respective pupil aperture;
independently processing each portion of illumination received by the one or more detectors to independently conduct defect detection for said at least two different illumination angles; and
determining, utilizing a computing system, a location of at least one defect of the sample utilizing information associated with the independently processed portions of illumination.

16. The method of claim 15, wherein illumination is sequentially received by the plurality of pupil apertures as the plurality of pupil apertures sequentially rotates through the illumination path.

17. The method of claim 15, wherein illumination is substantially simultaneously received by the plurality of pupil apertures.

18. The method of claim 17, further comprising:
directing a portion of illumination from each pupil aperture along the second portion of the illumination path to a respective field aperture utilizing a plurality of prisms disposed proximate to the plurality of pupil apertures.

19. The method of claim 18, further comprising:
receiving portions of illumination reflected, scattered, or radiated from the surface of the sample substantially simultaneously utilizing a plurality of detectors, each portion of illumination being associated with a respective pupil aperture.

20. The method of claim 19, further comprising:
directing portions of illumination reflected, scattered, or radiated from the surface of the sample to the plurality of detectors utilizing a plurality of prisms.

* * * * *